(12) United States Patent
Enegren et al.

(10) Patent No.: US 8,207,859 B2
(45) Date of Patent: *Jun. 26, 2012

(54) AUTOMOBILE PHYSIOLOGICAL MONITORING SYSTEM AND METHOD FOR USING THE SAME

(75) Inventors: Bradley J. Enegren, Moorpark, CA (US); Himanshu Patel, Tustin, CA (US); Bogdan Madzar, Santa Monica, CA (US); Richard K. Yoon, Northridge, CA (US); Ajit S. Narang, North Hills, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 450 days.

This patent is subject to a terminal disclaimer.

(21) Appl. No.: 12/423,964

(22) Filed: Apr. 15, 2009

(65) Prior Publication Data

US 2009/0267774 A1    Oct. 29, 2009

Related U.S. Application Data

(60) Provisional application No. 61/048,423, filed on Apr. 28, 2008.

(51) Int. Cl.
*G08B 23/00* (2006.01)
(52) U.S. Cl. ........... 340/573.1; 340/539.12; 340/426.11; 340/576; 180/272
(58) Field of Classification Search .............. 340/573.1, 340/539.12, 426.11, 426.13, 438, 439, 426.19, 340/576; 180/272, 275; 600/301, 300; 701/1; 455/556.1, 414.1

See application file for complete search history.

(56) References Cited

U.S. PATENT DOCUMENTS

| 4,664,127 A | 5/1987 | Ikeyama |
| 6,075,444 A * | 6/2000 | Sohege et al. ................. 340/576 |
| 6,104,296 A | 8/2000 | Yasushi et al. |

(Continued)

FOREIGN PATENT DOCUMENTS

| EP | 1618842 A1 | 1/2006 |
| GB | 2415036 A | 12/2005 |

OTHER PUBLICATIONS

Invitation to Pay Additional Fees and Partial International Search Report for PCT/US2009/040772.

(Continued)

*Primary Examiner* — Anh V La
(74) *Attorney, Agent, or Firm* — Medtronic MiniMed, Inc.

(57) ABSTRACT

An automobile monitoring system to monitor user body characteristics, includes at least one sensor to monitor at least one user body characteristic. The at least one sensor is operatively coupled to a body of a user to monitor the at least one user body characteristic while the user is operating an automobile. The at least one user body characteristic is at least a glucose level of the user's body. At least one transmitter is operatively coupled to the at least one sensor to communicate sensor data obtained from the at least one sensor while the user is operating the automobile. Automobile electronics are operatively coupled to the at least one transmitter to receive sensor data from the at least one sensor while the user is operating the automobile. The automobile electronics provide the sensor data to the user while the user is operating the automobile. A mobile telephone is operatively coupled to the automobile electronics, wherein the automobile electronics initiate a communication via the mobile telephone based on the sensor data received from the at least one sensor.

19 Claims, 3 Drawing Sheets

U.S. PATENT DOCUMENTS

| | | |
|---|---|---|
| 6,809,653 B1 | 10/2004 | Mann et al. |
| 2004/0240712 A1 | 12/2004 | Rowe et al. |
| 2005/0003470 A1 | 1/2005 | Nelson et al. |
| 2006/0193278 A1 | 8/2006 | Theimer |
| 2006/0258929 A1 | 11/2006 | Goode, Jr. et al. |
| 2006/0267781 A1 | 11/2006 | Coulter |
| 2006/0281980 A1 | 12/2006 | Randlov et al. |
| 2007/0112261 A1 | 5/2007 | Enegren et al. |
| 2007/0241915 A1 | 10/2007 | Basson et al. |

OTHER PUBLICATIONS

EP Examination Report for Application No. 06802296.1.

PCT International Search Report and Written Opinion for PCT/US2006/033156.

PCT International Search Report and Written Opinion for PCT/US2009/040772.

\* cited by examiner

AUTOMOBILE PHYSIOLOGICAL MONITORING SYSTEM AND METHOD FOR USING THE SAME

RELATED APPLICATION

This application claims priority from U.S. Provisional App. No. 61/048,423, filed Apr. 28, 2008, which is herein incorporated by reference in its entirety.

FIELD OF THE INVENTION

Embodiments of the present invention are directed to sensor monitoring systems and methods. Specifically, embodiments of the present invention are directed to connecting sensor monitoring systems to automobile electronics capable of initiating a communication based on sensor data.

BACKGROUND OF THE INVENTION

Diabetes is a disease in which the body does not produce or properly use insulin. Approximately 13 million people in the United States have been diagnosed with some form of diabetes. Type 1 diabetes results from the body's failure to produce insulin. Type 2 diabetes results from insulin resistance in which the body fails to properly use insulin. In order to effectively manage the disease, diabetics must closely monitor and manage their blood glucose levels through exercise, diet and medications. In particular, both Type 1 and Type 2 diabetics rely on insulin delivery and blood glucose monitoring to control their diabetes.

External infusion devices have been used to deliver medication to a patient as generally described in U.S. Pat. Nos. 6,554,798 and 6,551,276, which are specifically incorporated by reference herein in their entireties. In addition to delivering medication to a patient, other medical devices have been used to determine body characteristics by obtaining a sample of bodily fluid. A variety of implantable electrochemical sensors have been developed for detecting and/or quantifying specific agents or compositions in a patient's blood. For instance, glucose sensors have been developed for use in obtaining an indication of blood glucose levels in a diabetic patient. Such readings can be especially useful in monitoring and/or adjusting a treatment regimen that typically includes the regular administration of insulin to the patient. Thus, blood glucose readings are particularly useful in improving medical therapies with semi-automated medication infusion pumps of the external type and/or implantable type.

Monitoring blood glucose levels plays an integral role in the management and control of diabetes. Finger stick measurements, glucose sensors, and monitors have traditionally been used to check the blood glucose levels of diabetic patients. In recent years, continuous glucose monitoring systems have been developed utilizing the latest sensor technologies incorporating both implantable and external sensors as generally described in U.S. Pat. No. 5,391,250 entitled, "Method of Fabricating Thin Film Sensors", U.S. Pat. No. 6,484,046 entitled, "Electrochemical Analyte Sensor", and U.S. Pat. Nos. 5,390,671, 5,568,806 and 5,586,553, entitled, "Transcutaneous Sensor Insertion Set", all of which are specifically incorporated by reference herein in their entireties. Newer systems deliver the preciseness of finger stick measurements coupled with the convenience of not having to repeatedly prick the skin to obtain glucose measurements. These newer systems provide the equivalent of over 200 finger stick readings per day. Additionally, continuous glucose monitoring systems allow physicians and patients to monitor blood glucose trends of their body and suggest and deliver insulin based on each patient's particular needs. Accordingly, physicians and medical device companies are always searching for more convenient ways to keep diabetic patients aware of their blood glucose levels throughout the day.

SUMMARY OF THE INVENTION

An automobile monitoring system to monitor user body characteristics includes at least one sensor to monitor at least one user body characteristic. The at least one sensor is operatively coupled to a body of a user to monitor the at least one user body characteristic while the user is operating an automobile. The at least one user body characteristic is at least a glucose level of the user's body. At least one transmitter is operatively coupled to the at least one sensor to communicate sensor data obtained from the at least one sensor while the user is operating the automobile. Automobile electronics are operatively coupled to the at least one transmitter to receive sensor data from the at least one sensor while the user is operating the automobile. The automobile electronics provide the sensor data to the user while the user is operating the automobile. A mobile telephone is operatively coupled to the automobile electronics. The automobile electronics initiate a communication via the mobile telephone based on the sensor data received from the at least one sensor.

The sensor data received from the at least one sensor may indicate an emergency medical condition of the user. The mobile telephone may be operatively coupled to the automobile electronics via a wireless protocol. The communication initiated by the mobile telephone may be a voice call, a text message, or an e-mail. At least one monitor may be operatively coupled to the at least one transmitter to receive the sensor data. The at least one transmitter may communicate with the automobile electronics using at least one wireless protocol. The automobile electronics may include at least one of a GPS navigation system, a DVD entertainment system, an on-system computer, or a stereo system. Moreover, the automobile electronics may display sensor data to the user while the user is operating the automobile.

The automobile electronics may include default high blood glucose and low blood glucose thresholds for the glucose level while the user is operating the automobile. The automobile electronics may prevent ignition of the automobile when the sensor data is above the high blood glucose threshold or below the low blood glucose threshold. The automobile electronics may provide at least one warning when the sensor data is above the high blood glucose threshold or below the low blood glucose threshold while the user is operating the automobile. The automobile electronics may sound at least one alarm when the sensor data is above the high blood glucose threshold or below the low blood glucose threshold while the user is operating the automobile. The at least one alarm may provide at least one of audio, visual or tactile indications. The at least one sensor may be attached to the body of the user to sense the glucose level in bodily and/or interstitial fluids of the user while the user is operating the automobile. The at least one sensor may be attached to the body of the user to sense the glucose level on either a continuous, near continuous, or intermittent basis while the user is operating the automobile. The at least one sensor may be attached to the body of the user to sense the glucose level on a real-time basis while the user is operating the automobile. The automobile electronics may provide a warning to the user, while the automobile is in operation, to pull over the automobile and check the sensor readings prior to continued operation of the automobile. The automobile electronics may include the ability to access a communication technology that can send sensor data to an operational center to obtain assistance for the user. The automobile electronics may provide warnings of potential hypoglycemic or hyperglycemic situations while the user is operating the automobile.

An automobile monitoring system to monitor user body characteristics includes at least one sensor to monitor at least one user body characteristic. The at least one sensor is operatively coupled to a body of a user to monitor the at least one user body characteristic while the user is operating an automobile. The at least one user body characteristic is at least a glucose level of the user's body. At least one transmitter is operatively coupled to the at least one sensor to communicate sensor data obtained from the at least one sensor while the user is operating the automobile. Automobile electronics are operatively coupled to the at least one transmitter to receive sensor data from the at least one sensor while the user is operating the automobile. The automobile electronics provide the sensor data to the user while the user is operating the automobile. A global positioning system (GPS) is operatively coupled to the automobile electronics to determine a current location of the user. The automobile electronics limit the user from operating the automobile to travel beyond a distance based on the sensor data received from the at least one sensor.

The automobile electronics may provide a recommended destination before or at the distance for the user to travel to from the current location. The sensor data may include historical sensor data of the at least one user body characteristic. The sensor data received from the at least one sensor may indicate a hypoglycemic or a hyperglycemic condition of the user. The automobile electronics may permit the user to operate the automobile to travel beyond the distance to a second distance after making a stop before or at the distance. At least one monitor may be operatively coupled to the at least one transmitter to receive the sensor data. The at least one transmitter may communicate with the automobile electronics using at least one wireless protocol. The automobile electronics may include at least one of a GPS navigation system, a DVD entertainment system, an on-system computer, or a stereo system. The automobile electronics may display sensor data to the user while the user is operating the automobile.

The automobile electronics may include default high blood glucose and low blood glucose thresholds for the at least one glucose level while the user is operating the automobile. The automobile electronics may prevent ignition of the automobile when the sensor data is above the high blood glucose threshold or below the low blood glucose threshold. The automobile electronics may provide at least one warning when the sensor data is above the high blood glucose threshold or below the low blood glucose threshold while the user is operating the automobile. The automobile electronics may sound at least one alarm when the sensor data is above the high blood glucose threshold or below the low blood glucose threshold while the user is operating the automobile. The at least one alarm may provide at least one of audio, visual or tactile indications. The at least one sensor may be attached to the body of the user to sense the glucose level in bodily and/or interstitial fluids of the user while the user is operating the automobile. The at least one sensor may be attached to the body of the user to sense the glucose level on either a continuous, near continuous, or intermittent basis while the user is operating the automobile. The at least one sensor may be attached to the body of the user to sense the glucose level on a real-time basis while the user is operating the automobile. The automobile electronics may provide a warning to the user, while the automobile is in operation, to pull over the automobile and check the sensor readings prior to continued operation of the automobile. The automobile electronics may include the ability to access a communication technology that can send sensor data to an operational center to obtain assistance for the user. The automobile electronics may provide warnings of potential hypoglycemic or hyperglycemic situations while the user is operating the automobile.

An automobile monitoring system to monitor user body characteristics includes at least one sensor to monitor at least one user body characteristic. The at least one sensor is operatively coupled to a body of a user to monitor the at least one user body characteristic while the user is operating an automobile. The at least one user body characteristic is at least a glucose level of the user's body. At least one transmitter is operatively coupled to the at least one sensor to communicate sensor data obtained from the at least one sensor while the user is operating the automobile. Automobile electronics are operatively coupled to the at least one transmitter to receive sensor data from the at least one sensor while the user is operating the automobile. The automobile electronics provide the sensor data to the user while the user is operating the automobile. A global positioning system (GPS) is operatively coupled to the automobile electronics to determine a current location of the user. The automobile electronics provide a nearest destination from the current location of the user for the user to travel to based on the sensor data received from the at least one sensor.

The nearest destination may be one of a hospital, a pharmacy, a medical office, a convenience store, a market, a rest stop, and a restaurant. At least one monitor may be operatively coupled to the at least one transmitter to receive the sensor data. The at least one transmitter may communicate with the automobile electronics using at least one wireless protocol. The automobile electronics may include at least one of a GPS navigation system, a DVD entertainment system, an on-system computer, or a stereo system. The automobile electronics may display sensor data to the user while the user is operating the automobile.

The automobile electronics may include default high blood glucose and low blood glucose thresholds for the glucose level while the user is operating the automobile. The automobile electronics may prevent ignition of the automobile when the sensor data is above the high blood glucose threshold or below the low blood glucose threshold. The automobile electronics may provide at least one warning when the sensor data is above the high blood glucose threshold or below the low blood glucose threshold while the user is operating the automobile. The automobile electronics may sound at least one alarm when the sensor data is above the high blood glucose threshold or below the low blood glucose threshold while the user is operating the automobile. The at least one alarm may provide at least one of audio, visual or tactile indications. The at least one sensor may be attached to the body of the user to sense the glucose level in bodily and/or interstitial fluids of the user while the user is operating the automobile. The at least one sensor may be attached to the body of the user to sense the glucose level on either a continuous, near continuous, or intermittent basis while the user is operating the automobile. The at least one sensor may be attached to the body of the user to sense the glucose level on a real-time basis while the user is operating the automobile. The automobile electronics may provide a warning to the user, while the automobile is in operation, to pull over the automobile and check the sensor readings prior to continued operation of the automobile. The automobile electronics may include the ability to access a communication technology that can send sensor data to an operational center to obtain assistance for the user. The sensor data received from the at least one sensor may indicate a hypoglycemic or a hyperglycemic condition of the user.

DETAILED DESCRIPTION

Figure 1:
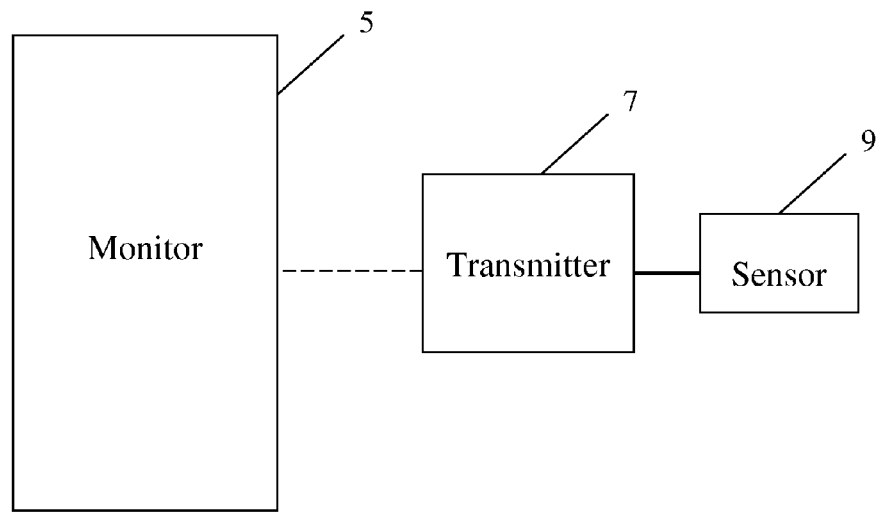
FIG. 1 illustrates a continuous glucose monitoring system including a sensor, transmitter, and monitor.

As shown in the drawings for purposes of illustration, the invention is embodied in a glucose monitoring system for use with an automobile vehicle. In particular embodiments of the invention, a real-time continuous glucose monitoring system communicates with electronics of an automobile to display real-time glucose sensor measurements and provide information related to high and low blood glucose levels to the patient in addition to blood glucose related trends using graphs and other analytical models. It will be recognized that further embodiments of the invention may be used with other types of sensors to determine the levels of other agents, characteristics or compositions, such as hormones, cholesterol, medication concentrations, pH, oxygen saturation, viral loads (e.g., HIV), heart rate, cardiac rhythm, or the like.

In particular embodiments of the invention, a glucose monitoring system, as shown in FIG. 1, displays real-time glucose values to the patient. In these embodiments, the glucose monitoring system includes a sensor 9 for measuring an agent such as blood glucose levels and the like. In preferred embodiments, the sensor is a subcutaneously inserted electrochemical sensor that generates varying levels of electrical current proportional to the amount of glucose in a person's body. The current readings can then be translated into a blood glucose value that is understandable to a user. Example of such a sensor is described in U.S. Pat. No. 6,809,653 entitled, "Telemetered Characteristic Monitor System And Method Of Using The Same", which is specifically incorporated by reference herein in its entirety. However, any type of glucose sensor that can produce a glucose value would work with the system described in FIG. 1. In preferred embodiments, the sensor 9 includes a processing unit that translates the sensor readings into blood glucose readings. The processing unit is then linked to a transmitter 7 which would transmit the glucose values to a glucose monitor 5 that is capable of displaying the glucose values. In certain embodiments, the sensor and transmitter may be integrated into one unit or the sensor may have a built-in transmitter. The transmitter 7 provides the necessary electronics to communicate the sensor data to the glucose monitor 5. In still further embodiments, the transmitter 7 attached to the sensor 9 may also serve as a receiver to receive data from the monitor 5, a computer, an external infusion device or the like. Example of a sensor and transmitter combination may be found in commonly assigned U.S. patent application Ser. No. 12/056,651 entitled "Glucose Sensor Transceiver", which is specifically incorporated by reference herein in its entirety.

The monitor 5 may include an LCD to display the sensor data. In other embodiments, the monitor 5 may include an alarm and/or multiple alarms that activate when high and/or low blood glucose levels are detected. These alarms may be in the form of audible, visual, and/or tactile indications. In other embodiments, the alarms may activate upon user programmed instances such as an abnormal highs and/or lows in glucose levels for a particular time of the day.

Figure 2:
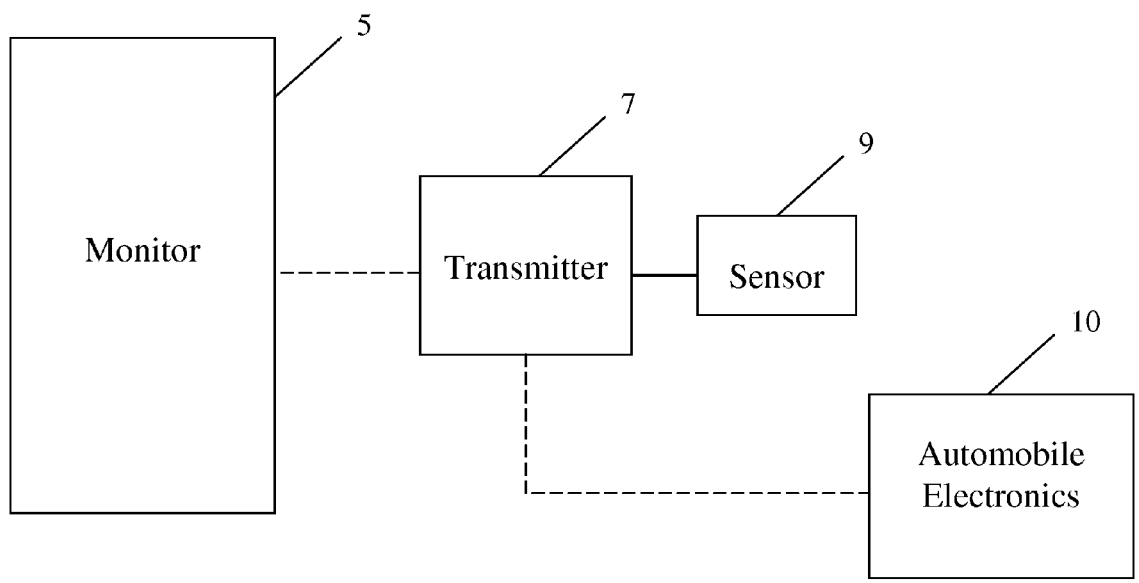
FIG. 2 illustrates an automobile monitoring system utilizing the glucose monitoring system of FIG. 1 according to embodiments of the present invention.

In other embodiments, the glucose monitoring system may be adapted to communicate to automobile electronics. In particular embodiments, as shown in FIG. 2, the sensor 9 and transmitter 7 communicate directly with automobile electronics 10 including GPS navigation system, DVD entertainment system, on-system computer, stereo system or the like. In these embodiments, the automobile electronics may function as the traditional glucose monitor and display the sensor data to the patient on the dashboard, LCD screen located in the automobile, GPS navigation screen, DVD screen, stereo screen or the like. In additional embodiments, the automobile electronics may include algorithms to display sensor derived graphs and/or charts based on the patient's sensor data.

Figure 3:
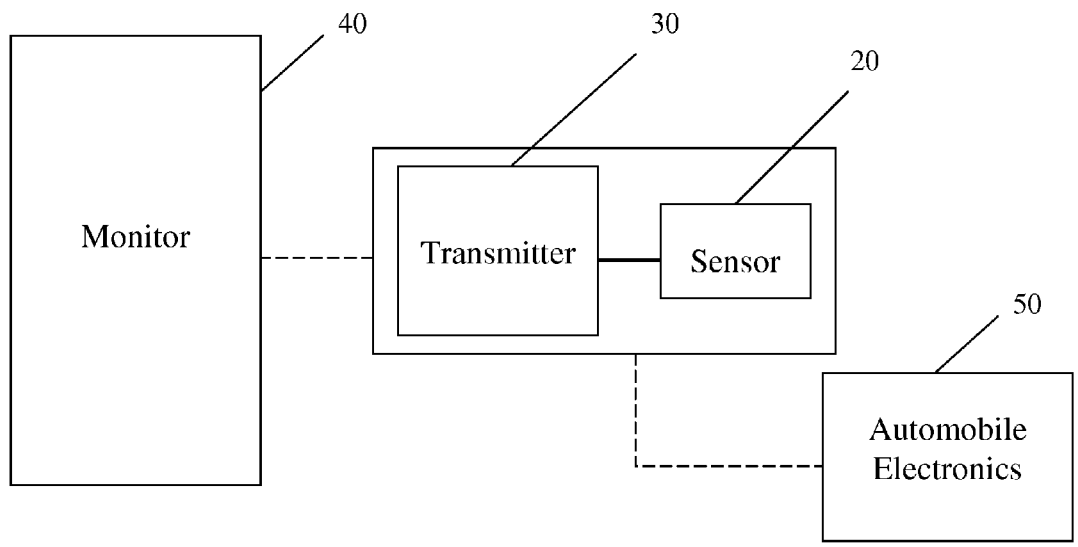
FIG. 3 shows a block diagram of an automobile monitoring system according to embodiments of the present invention.

In further embodiments, as shown in FIG. 3, the glucose sensor 20 and transmitter 30 may communicate directly with the glucose monitor 40 and/or the automobile electronics 50 as described above. In particular embodiments, the transmitter may communicate using wireless protocols such as Bluetooth, Infrared, Radio Frequency, 802.11a, 802.11b, 802.11g, or the like. The transmitter may be equipped to handle multiple communication protocols and/or a single communication protocol. In still additional embodiments, the transmitter may communicate with the glucose monitor and or automobile electronics via a wired connection. The wire may either run from the transmitter into the glucose monitor and/or a port installed in the automobile's dashboard, GPS navigation system, DVD entertainment system, on-system computer, stereo system or the like. The wired port may use a standard computer connector port including serial, parallel, USB, FireWire (IEEE 1394), or the like.

In additional embodiments, the glucose monitoring system may connect to the automobile electronics using any of the communication protocols described above. In these embodiments, the sensor and transmitter may connect the moment the patient unlocks the automobile door, enters the automobile, places the key in the ignition or the like. Upon connection, algorithms may be in place that allow the automobile electronics to prevent ignition of the automobile if sensor data indicates glucose levels above and/or below particular threshold values. Alternatively, in other embodiments, a warning may be displayed to the patient on the monitor itself and/or the automobile electronics notifying the user of high and/or low values.

In other embodiments, the automobile electronics may provide indications, data, graphs and/or trends on the dashboard, LCD screen located in the automobile, GPS navigation screen, DVD screen, stereo screen or the like. In alternative embodiments, the automobile electronics may provide alarms based on factory and/or user specified occurrences. Examples include high blood glucose levels, low blood glucose levels and the like. The alarms may come in the form of audio, visual, and/or tactile indications.

In other embodiments, the glucose monitoring system may provide warnings and/or alarms to the patient while the patient is operating the automobile. These warnings and/or alarms may be based on high blood glucose readings, low blood glucose readings, or the like. In the event a warning and/or alarm is displayed to the patient while the automobile is in operation, the patient may be prompted to pull over the automobile and check the sensor readings prior to continued operation of the automobile. The safety factors associated with such a system provide diabetic patients and the public with advanced warnings of potential hypo- and/or hyperglycemic situations.

Figure 4:
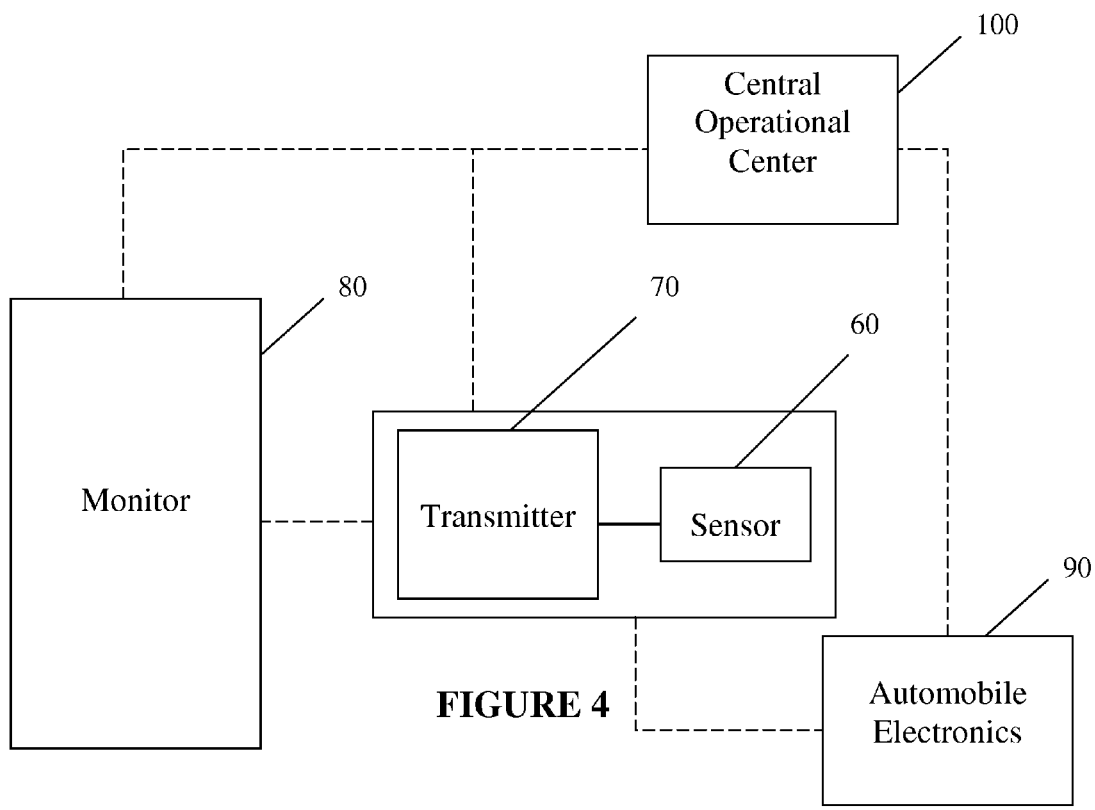
FIG. 4 shows a block diagram of an automobile monitoring system according to embodiments of the present invention.

In still further alternative embodiments, as shown in FIG. 4, automobiles equipped with OnStar™ technology and/or any other similar communication protocols may transmit the sensor data to a central operational center. In particular, the transmitter 70, monitor 80 and/or the automobile electronics 90 may communicate the sensor data to a central location 100. These locations may be operational centers where an operator may assist the patient with any medical emergencies based on high and/or low blood glucose readings. In further embodiments, the transmitter 70, monitor 80 and/or automobile electronics 90 may transmit the sensor data to a specific medical center allowing selected physicians to monitor the sensor data, provide suggestions on treatment regimens, and/or assist the patient with overcoming dangerously high or low blood glucose levels. In still additional embodiments, the OnStar™ technology may be utilized to contact the appropriate protective services based on dangerously high and/or low blood glucose readings. Paramedics, police and/or fire departments may be contacted depending on the severity of the situation.

In further embodiments, for vehicles not equipped with OnStar™ type technology, the transmitter, monitor and/or the automobile electronics may transmit the data to a central location using standardized wireless protocols including Wi-Fi™, GPS satellite, cellular network, or the like.

An illustrative automobile monitoring system is described in U.S. Pat. App. No. 2007/0112261, published May 17, 2007, to Enegren et al., and is entitled, "Automobile Glucose Sensor Monitoring System and Method for Using the Same", which is herein incorporated by reference in its entirety.

Figure 5:
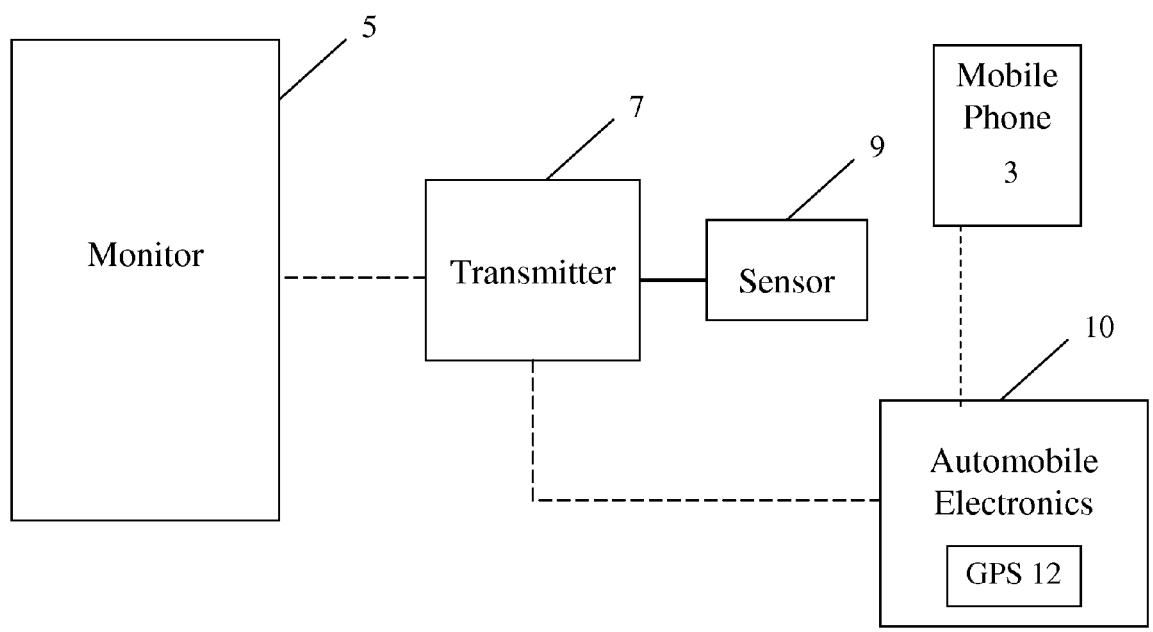
FIG. 5 illustrates an automobile monitoring system utilizing the glucose monitoring system of FIG. 1 according to embodiments of the present invention.

FIG. 5 illustrates an automobile monitoring system utilizing the glucose monitoring system of FIG. 1 according to embodiments of the present invention. According to embodiments of the present invention, physiological monitoring systems, such as glucose monitoring systems, are connected to automobile electronics. Such physiological systems include communication capabilities to relay physiological data to handheld monitors and/or automobile electronics. The connection allows physiological information to be displayed on electronics already residing in automobiles, including GPS systems, DVD systems, on-system computers, stereos, Bluetooth communication systems, and the like. Sensors may connect to different types of motorized vehicles including cars, boats, trucks, motorcycles, planes, and the like. The sensors may be attached to the body of a user to sense, for example, glucose levels in the bodily or interstitial fluids of the user while the user is operating the automobile. In addition, embodiments of the present invention are applicable to other types of medical devices, and are not limited to sensors. Examples of other medical devices include insulin infusion pumps, pacemakers, and the like.

According to embodiments of the present invention, the monitoring systems may include predefined thresholds of physiological values. The monitoring system, for example, may be programmed with default high and low blood glucose thresholds for identifying hyperglycemic and/or hypoglycemic conditions. Based on these thresholds, the sensor monitoring system may utilize, for example, an automobile's Bluetooth communication system 10 to initiate a cellular telephone call through a paired cellular/mobile phone 3, or similar communication device. A phone call may be placed to a caregiver, doctor, hospital, police, ambulance, or the like. According to embodiments of the present invention, a text message (SMS) or e-mail may be sent using the Bluetooth-paired cell phone 3 to a specific phone number or e-mail address. Any suitable communication protocols other than Bluetooth may be utilized, too. The voice call, text message, and/or e-mail may be initiated, for example, when the sensor data indicates that the user is in, or is approaching, an emergency medical condition and may require immediate medical attention.

Moreover, according to embodiments of the present invention, program functions of medical devices with the user, for example, monitoring systems such as glucose sensor systems 9, may be adjusted by the driver/user of the vehicle using the automobile's on-system computer 10, i.e., Ford Motor Company's SYNC™ system. Alternatively, program functions may be adjusted by the sensor monitoring system's 9 handheld monitoring device/controller 5 (if included). In other embodiments, program functions may be adjusted by either device or only one device. In still other embodiments, program functions may be adjusted by a central server (see, e.g., central operational center 100 in FIG. 4 above) that communicates with the automobile through a built-in GPS/safety system 10, similar to the OnStar™ or BMW Assist™ systems.

According to embodiments of the present invention, a medical device with the user, for example, a glucose sensor system 9, may link up with the automobile on-system computer 10 (e.g., Ford's SYNC™ system) and utilize the on-system computer's 10 microphone, for example, for the user to issue voice commands to operate and control the medical device with the user. For example, if the medical device is an insulin infusion pump, the user inside the car (be it the driver or passenger) may issue a voice command through the on-system computer 10 to control and operate the insulin infusion pump (e.g., to deliver a bolus, display the status of the pump on the display screen of the on-system computer 10, etc.) Additionally, if the on-system computer 10 has a communication device (e.g., a paired cellular/mobile phone 3), the on-system computer 10 may receive calls from people remote from the user and the remote callers may also issue voice commands to operate and control the medical device with the user that is linked up with the on-system computer 10. Alternatively, a Bluetooth (or any suitable protocol) headset may be paired with a medical device, e.g., an insulin infusion pump, and the user may also issue voice commands to the medical device via the headset.

Moreover, if the on-system computer 10 has a communication interface (via cellular/mobile phone 3, wireless modem, WiFi, GPS, radio, satellite, OnStar™, etc.), others may also remotely access the medical device that is with the user linked up with the on-system computer 10 to control and operate the medical device, through for example, a Web site on the Internet, a PC, a mobile phone, or the like.

According to embodiments of the present invention, an automobile on-system computer 10 (e.g., Ford's SYNC™ system) may control all functions of medical devices and/or physiological sensors 9 in the vicinity of the automobile. In these embodiments, the physiological sensor 9 may not include a handheld monitor 5 for programming. Instead, the physiological sensor 9 may include a communication device to communicate (or pair) with an automobile on-system computer 10, and all subsequent programming, control, and operation of the sensor 9 is handled by the automobile's computer system 10.

In still further embodiments, the sensor may also include a handheld monitor 5, where programming may take place by either a handheld monitor/controller 5, the automobile on-system computer 10, or by either device.

In some embodiments, communication between the physiological sensor 9 and the automobile electronics 10 may be handled through wireless means. In particular embodiments, no protocol conversion is necessary because the physiological sensor 9 includes the communication functionality that is already available in the vehicle. These embodiments include Bluetooth-like functionality (or similar standardized wireless protocols). If the sensor 9 includes Bluetooth capability, for example, the sensor 9 may communicate directly with the vehicle without the need for protocol conversion.

In other embodiments, the sensor 9 communicates directly with a USB receiver that receives data from the sensor 9 via a proprietary communication protocol. The USB receiver may plug directly into the automobile's on-system computer 10 to transfer data received from the physiological sensor 9. In some embodiments, the USB receiver functions as a wireless relay device by receiving data from a sensor 9 using a proprietary communication protocol, and then wirelessly sending the data to the automobile using, for example, standard Bluetooth connections. In other embodiments, the USB receiver transfers the data directly through the USB connection on the automobile on-system computer 10.

In some embodiments, a central server (see, e.g., central operational center 100 in FIG. 4 above) may include a patient's sensor history and may transmit to and display that data on the automobile's built-in display unit 10 (the navigation/GPS screen, the DVD screen, vehicle information screen, and the like). In the case of a glucose sensor 9, the central server may display blood glucose values from, for example, the past two weeks. Other time ranges may be available including the previous day extending all the way to previous years. Future predicted blood glucose values may also be displayed utilizing various blood glucose prediction algorithms and the like. Descriptions of systems utilizing predictive blood glucose algorithms may be found in U.S. Pat. No. 6,558,351 to Steil et al., entitled, "Closed Loop System for Controlling Insulin Infusion", which is herein incorporated by reference in its entirety.

In other embodiments, the central server may operate, program, and control the sensor monitoring system 9 (or other nearby medical devices). In these embodiments, the central server may adjust settings on a device based on specific situations. Emergency control may be required if the driver of the automobile enters into a dangerous physical state based on readings received from the sensors 9.

In some embodiments, if the automobile includes a GPS navigation system 12, the central server may be able to locate the patient in times of emergency situations—i.e., if the patient goes into a hypo- or hyperglycemic state and can no longer control the vehicle and/or respond to communications. In other instances, if a patient tends to go hypoglycemic, the on-system computer 10 may prevent the driver from traveling beyond a certain distance from a hospital, home, or other location. These distance ranges and sensor thresholds may be programmed by the patient, the doctor, or by the central server. According to embodiments of the present invention, the automobile electronics 10 may provide a recommended destination that is before, or at, the maximum distance permitted for the user to drive based on at least one of the sensor data received from the sensor 9, the user's current location, and the location of a particular establishment, such as a hospital, doctor's office, market/convenience store, the homes of the user/relatives/friends, restaurant, etc. Historical sensor data may be taken into account to determine the distance permitted for the user to drive. According to alternative embodiments of the present invention, the automobile electronics 10 may permit the user to operate the automobile to travel beyond the maximum distance to a second distance after making a stop before or at the maximum distance (for example, making a "pit stop" for 15-minutes at a convenience store to take a break and buy some orange juice). Multiple waypoints with breaks/pit stops in between may permit a user to travel a long distance safely that would be otherwise not advisable for the user to undertake.

In other embodiments, if the automobile also includes Internet connectivity, the sensor readings may be uploaded directly to an online patient management tool (like Medtronic MiniMed's CareLink® system). Based on timing and patient readings, the automobile's on-system computer 10 may provide the patient with important information about his/her medical device usage. Some information may include a reminder to order additional medical supplies. In further embodiments, the system 10 may also recommend where to pick up the medical devices by locating the patient via the automobile's GPS system 12.

Internet connectivity may be built into the automobile, similar to GPS navigation integration. Alternatively, the driver of the vehicle may utilize an Internet connection available on a cellular/mobile phone 3 to upload/download information online. In still other embodiments, the cellular/mobile phone's 3 Internet connection may be tethered to the automobile electronics 10 for direct integration (i.e., via a Bluetooth connection).

In further embodiments, the monitoring system may use the GPS and/or Internet functionality to determine the location of the nearest hospital or restaurant. In the case of a diabetic patient, if the monitoring system senses that the patient needs additional insulin (hyperglycemic) or needs additional carbohydrates (hypoglycemic), or has a medical or non-medical condition requiring attention, the GPS navigation system 12 may be utilized to locate the closest hospital, pharmacy, medical office, convenience store, market, rest stop, or restaurant, etc., so the patient can act immediately. For example, if the monitoring system determines that the user is experiencing a hypoglycemic condition, it may prompt the user to drive 0.3 miles down the same street to the next convenience store and purchase some orange juice, or the like.

In other embodiments of the invention, the monitoring system—when connected to automobile electronics 10—may allow potential drivers to obtain a drivers license. In some countries, for example, a person may not obtain a driver's license because they suffer from a disease like diabetes. In such countries, the embodiments described in the present application may allow such individuals to obtain a driver's license because the automobile would only operate if the individual's monitored physiological characteristics were in normal ranges. As an example, a diabetic could operate the automobile so long as their blood glucose levels were in acceptable ranges as identified by their continuous glucose monitoring system, which is connected to the automobile electronics 10.

In other embodiments, if the driver of the automobile were to undertake a long drive, the on-system computer 10 may allow the patient to program the location and recommend pit stops based on the patient's blood glucose history. The system may analyze the patient's supplies, blood glucose history, and destination to recommend where the patient should stop and take a break. The patient may resume his/her journey after a period of time has lapsed. As discussed above, the patient may set up multiple waypoints (to take breaks, eat, etc.) to safely reach the ultimate destination.

In further embodiments, the monitoring system and automobile electronics 10 may include various alerts to identify specific conditions. In some embodiments, a silent alert may activate and be transmitted to a central server. These silent alerts include a reminder that the patient needs to order new supplies, or may be simply a status check on how the monitoring system is functioning. In other embodiments, specific conditions may be monitored based on predetermined doctor requests. Upon receipt of the silent alerts, the central server may review the received data and determine if additional action is necessary. If additional action is necessary, the central server may send a text message (SMS), or other communication, to the patient, a doctor, the vehicle, or caregiver. In other embodiments, the central server may require the automobile electronics 10 to display a message on the automobile's display unit and/or on the sensor's monitor 5.

In still further embodiments, standardized alerts may be displayed on the automobile electronics' 10 display units including high and low blood glucose levels and the like. Again, other health conditions may be monitored in these systems including heart rate, levels of other agents, characteristics or compositions, such as hormones, cholesterol, medication concentrations, pH, oxygen saturation, viral loads and the like.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. An automobile monitoring system to monitor user body characteristics, comprising:
   at least one sensor to monitor at least one user body characteristic, wherein the at least one sensor is operatively coupled to a body of a user to monitor the at least one user body characteristic while the user is operating an automobile, the at least one user body characteristic is at least a glucose level of the user's body, and the at least one sensor is attached to the body of the user to sense the glucose level on either a continuous, near continuous, or intermittent basis while the user is operating the automobile;
   at least one transmitter operatively coupled to the at least one sensor to communicate sensor data obtained from the at least one sensor while the user is operating the automobile;
   automobile electronics operatively coupled to the at least one transmitter to receive sensor data from the at least one sensor while the user is operating the automobile, wherein the automobile electronics provide the sensor data to the user while the user is operating the automobile; and
   a mobile telephone operatively coupled to the automobile electronics, wherein the automobile electronics include default high blood glucose and low blood glucose thresholds for the glucose level while the user is operating the automobile, and the automobile electronics initiate a communication via the mobile telephone based on the sensor data received from the at least one sensor when the sensor data is above the high blood glucose threshold or below the low blood glucose threshold.

2. The automobile monitoring system of claim 1, wherein the sensor data received from the at least one sensor indicates an emergency medical condition of the user.

3. The automobile monitoring system of claim 1, wherein the mobile telephone is operatively coupled to the automobile electronics via a wireless protocol.

4. The automobile monitoring system of claim 1, wherein the communication is a voice call.

5. The automobile monitoring system of claim 1, wherein the communication is a text message.

6. The automobile monitoring system of claim 1, wherein the communication is an e-mail.

7. The automobile monitoring system of claim 1, further including:
   at least one monitor operatively coupled to the at least one transmitter to receive the sensor data.

8. The automobile monitoring system of claim 1, wherein the at least one transmitter communicates with the automobile electronics using at least one wireless protocol.

9. The automobile monitoring system of claim 1, wherein the automobile electronics include at least one of a GPS navigation system, a DVD entertainment system, an on-system computer, or a stereo system, and wherein the automobile electronics display sensor data to the user while the user is operating the automobile.

10. The automobile monitoring system of claim 1, wherein the automobile electronics further prevent ignition of the automobile when the sensor data is above the high blood glucose threshold or below the low blood glucose threshold.

11. The automobile monitoring system of claim 1, wherein the automobile electronics provide at least one warning when the sensor data is above the high blood glucose threshold or below the low blood glucose threshold while the user is operating the automobile.

12. The automobile monitoring system of claim 1, wherein the automobile electronics sound at least one alarm when the sensor data is above the high blood glucose threshold or below the low blood glucose threshold while the user is operating the automobile.

13. The automobile monitoring system of claim 12, wherein the at least one alarm provides at least one of audio, visual or tactile indications.

14. The automobile monitoring system of claim 1, wherein the at least one sensor is attached to the body of the user to sense the glucose level in bodily fluids of the user while the user is operating the automobile.

15. The automobile monitoring system of claim 1, wherein the at least one sensor is attached to the body of the user to sense the glucose level in interstitial fluid contained in the body of the user while the user is operating the automobile.

16. The automobile monitoring system of claim 1, wherein the at least one sensor is attached to the body of the user to sense the glucose level on a real-time basis while the user is operating the automobile.

17. The automobile monitoring system of claim 1, wherein the automobile electronics provide a warning to the user, while the automobile is in operation, to pull over the automobile and check the sensor readings prior to continued operation of the automobile.

18. The automobile monitoring system of claim 1, wherein the automobile electronics further include the ability to access a communication technology that can send sensor data to an operational center to obtain assistance for the user.

19. The automobile monitoring system of claim 1, wherein the automobile electronics provide warnings of potential hypoglycemic or hyperglycemic situations while the user is operating the automobile.

* * * * *